(12) United States Patent
Amemiya

(10) Patent No.: US 8,568,783 B2
(45) Date of Patent: Oct. 29, 2013

(54) HYDROPHILIZED SUBSTRATE, DISPERSION, AND MAKING METHOD

(75) Inventor: Masahiro Amemiya, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 13/422,461

(22) Filed: Mar. 16, 2012

(65) Prior Publication Data

US 2012/0172611 A1   Jul. 5, 2012

Related U.S. Application Data

(62) Division of application No. 12/649,720, filed on Dec. 30, 2009, now abandoned.

(30) Foreign Application Priority Data

Jan. 9, 2009   (JP) .................................. 2009-003440

(51) Int. Cl.
| | | |
|---|---|---|
| A61K 8/28 | (2006.01) |
| A61K 8/29 | (2006.01) |
| A61K 8/36 | (2006.01) |
| C07F 7/18 | (2006.01) |
| C07F 3/06 | (2006.01) |
| C07F 1/04 | (2006.01) |
| C07F 1/06 | (2006.01) |
| C07F 7/28 | (2006.01) |

(52) U.S. Cl.
USPC ........... 424/490; 556/438; 556/463; 556/465; 556/482

(58) Field of Classification Search
USPC ................... 424/490; 556/438, 463, 465, 482
See application file for complete search history.

(56) References Cited

U.S. PATENT DOCUMENTS

2005/0208087 A1*  9/2005  Kuerzinger et al. .......... 424/405

FOREIGN PATENT DOCUMENTS

WO    WO 2005/098910 A2  *  10/2005

* cited by examiner

Primary Examiner — Richard Schnizer
Assistant Examiner — Alma Pipic
(74) Attorney, Agent, or Firm — Oblon, Spivak, McClelland, Maier & Neustadt, L.L.P.

(57) ABSTRACT

A powder is hydrophilized by treating surfaces of particles with a hydrolyzable silyl group-containing acid anhydride compound, dispersing the surface treated particles in water, adding a base, and heating the dispersion for thereby hydrolyzing the acid anhydride moiety to open its ring and neutralizing the resultant carboxylic acid with the base. The hydrophilized powder is fully dispersible in aqueous media.

17 Claims, No Drawings

HYDROPHILIZED SUBSTRATE, DISPERSION, AND MAKING METHOD

CROSS-REFERENCE TO RELATED APPLICATION

This application is a Divisional of U.S. application Ser. No. 12/649,720, filed on Dec. 30, 2009, pending.

This non-provisional application claims priority under 35 U.S.C. §119(a) on Patent Application No. 2009-003440 filed in Japan on Jan. 9, 2009, the entire contents of which are hereby incorporated by reference.

TECHNICAL FIELD

This invention relates to a hydrophilized substrate, typically powder, which is obtained by surface treating with a hydrolyzable silyl group-containing acid anhydride compound, hydrolyzing the acid anhydride moiety to open its ring and neutralizing the resultant carboxylic acid with a base. It also relates to a dispersion of the hydrophilized powder, and a method for preparing the same.

BACKGROUND ART

For the surface treatment of substrates, many treating agents are used for various purposes. The agent and method for use in surface treatment are generally selected in accordance with the surface properties of a substrate to be treated and other factors. For example, lipophilic treatment with lubricants and metal soaps, hydrophilic treatment with surfactants and water-soluble polymers, and water/oil repellent treatment with silicone fluids are known.

Herein hydrophilic treatment is of concern. When powder particles are dispersed in an aqueous medium, for example, particles tend to agglomerate together due to the electricity and polarity on particle surfaces, trace impurities, and the like. Prior attempts to minimize agglomeration in aqueous media include hydrophilic treatment on particle surfaces. However, hydrophilic treatments with conventional surfactants and water-soluble polymers are not fully effective. When a composition is loaded with powder treated with such an agent, there is a likelihood that the treating agent may dissociate from particles in the system, leading to color variations, a color difference between appearance and coat, and a decreasing degree of dispersion with time, which is detrimental to the applicability of the composition. Depending on the identity of surfactant, the composition becomes irritant to the skin and thus undesired for use in cosmetics.

JP-A H09-2815 discloses that the surface of smectite clay mineral is rendered hydrophilic by treatment with a polyether-modified silane compound having a hydrolyzable silyl group. Since the hydrolyzable silyl group forms a chemical bond with the particle surface, this method overcomes the problem that the treating agent may dissociate from particles in the system. The method achieves a degree of hydrophilicity which is still unsatisfactory. For example, when the method is applied to the surface treatment of titanium oxide powder, the treated powder is not fully dispersible in aqueous media.

CITATION LIST

Patent Document 1: JP-A H09-2815

SUMMARY OF INVENTION

An object of the invention is to provide a hydrophilized substrate having a sufficient degree of hydrophilicity, and specifically, a hydrophilized substrate, typically in powder form, which is fully dispersible in an aqueous medium and devoid of skin irritation, a dispersion of hydrophilized powder, and methods for preparing the hydrophilized substrate and the dispersion.

The inventor has found that a hydrophilized substrate is obtained by surface treating a substrate, specifically powder, with a hydrolyzable silyl group-containing acid anhydride compound, hydrolyzing the acid anhydride moiety for ring opening, and neutralizing the resultant carboxylic acid with a base. The thus treated substrate exhibits excellent hydrophilicity. Especially, the hydrophilic treated powder is fully dispersible in water and stable in dispersion and thus useful as an additive to cosmetics and paints.

In a first aspect, the invention provides a hydrophilized substrate having on its surface a surface treatment layer comprising a hydrolyzable silyl group-containing acid anhydride compound wherein carboxylic acid resulting from ring-opening of the acid anhydride moiety is partially or completely neutralized with a base. The acid anhydride compound has the general formula (1):

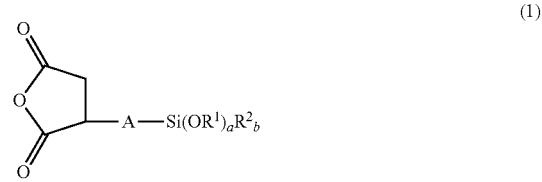

wherein $R^1$ is hydrogen or $C_1$-$C_6$ alkyl, $R^2$ is each independently an organic group selected from the group consisting of $C_1$-$C_{30}$ alkyl, aryl, aralkyl, and fluoroalkyl, A is a straight or branched $C_2$-$C_6$ alkylene, a is an integer of 1 to 3, b is an integer of 0 to 2, and a+b=3.

In a preferred embodiment, the acid anhydride compound has the general formula (2):

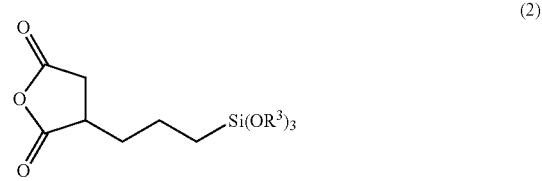

wherein $R^3$ is methyl or ethyl.

In a preferred embodiment, the base is selected from the group consisting of NaOH, KOH, ammonia, monoethanolamine, diethanolamine, triethanolamine, and triethylamine, and mixtures comprising at least two of the foregoing. The base is preferably used in an equivalent amount which is 0.1 to 2 times the total equivalent amount of carboxylic acid resulting from ring-opening of the acid anhydride moiety.

Most often, the substrate is a powder, which is preferably an inorganic powder, and more preferably zinc oxide or titanium oxide.

In a preferred embodiment, the hydrophilized powder is obtained by treating surfaces of powder particles with the hydrolyzable silyl group-containing acid anhydride compound having the general formula (1) in an amount of 0.01 to 30 parts by weight per 100 parts by weight of the powder.

In a second aspect, the invention provides a dispersion comprising the hydrophilized powder dispersed in water, a water-soluble solvent, or a mixture of water and a water-soluble solvent.

In a third aspect, the invention provides a method for preparing a hydrophilized substrate, comprising the steps of (A) treating a surface of a substrate with a hydrolyzable silyl group-containing acid anhydride compound having formula (1), (B) immersing the surface treated substrate in water or a mixture of water and a solvent, adding a base thereto, and heating the liquid for thereby hydrolyzing the acid anhydride moiety to open its ring and neutralizing the resultant carboxylic acid, and (C) removing water and the solvent until the substrate is dry. Most often, the substrate is a powder.

Thus, the invention also provides a method for preparing a dispersion of hydrophilized powder, comprising the steps of (A) treating surfaces of powder particles with a hydrolyzable silyl group-containing acid anhydride compound having formula (1), (B) immersing the surface treated powder in water or a mixture of water and a solvent, adding a base thereto, and heating the liquid for thereby hydrolyzing the acid anhydride moiety to open its ring and neutralizing the resultant carboxylic acid, and (C) feeding the liquid from step (B) to a dispersing machine for finely dispersing the powder particles.

ADVANTAGEOUS EFFECTS OF INVENTION

Since a surface treatment layer wherein carboxylic acid resulting from ring-opening of the acid anhydride moiety of a hydrolyzable silyl group-containing acid anhydride compound is partially or completely neutralized with a base is present on the substrate surface, the hydrophilized substrate exhibits excellent hydrophilicity. The hydrophilic treated substrate, specifically hydrophilic treated powder is fully dispersible in aqueous media and devoid of skin irritation and other unwanted effects.

DESCRIPTION OF EMBODIMENTS

As used herein, the term "powder" is interchangeable with the term "particles" because the powder consists of particles. In this sense, the term "powder surface" refers to surfaces of particles.

The surface treating agent used herein is a hydrolyzable silyl group-containing acid anhydride compound having the general formula (1).

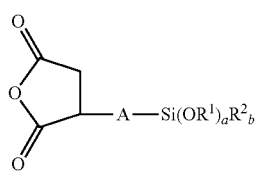

(1)

Herein $R^1$ is hydrogen or a $C_1$-$C_6$ alkyl group such as methyl, ethyl, propyl or butyl, with methyl and ethyl being preferred. $R^2$ is each independently an organic group selected from among $C_1$-$C_{30}$, preferably $C_1$-$C_{10}$, alkyl groups such as methyl, ethyl, propyl and butyl, aryl groups such as phenyl, aralkyl groups, and fluoroalkyl groups such as 3,3,3-trifluoropropyl, with methyl being preferred. A is a straight or branched alkylene group of 2 to 6 carbon atoms, preferably 2 to 4 carbon atoms, most preferably 3 carbon atoms. The subscript "a" is an integer of 1 to 3, preferably 2 or 3, and most preferably 3; "b" is an integer of 0 to 2, preferably 0 or 1, and most preferably 0; and a+b=3.

The preferred acid anhydride compound has the general formula (2):

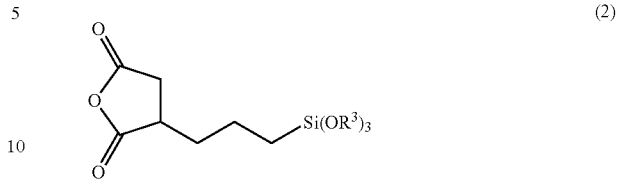

(2)

wherein $R^3$ is methyl or ethyl.

Below described is the method of treating a substrate so as to render its surface hydrophilic using the hydrolyzable silyl group-containing acid anhydride compound.

The substrate used herein is not particularly limited as long as its surface must be rendered hydrophilic. The substrate may be either organic or inorganic. The shape is not particularly limited and includes plate, sheet, mass, powder and the like, with the powder consisting of particles being most preferred.

Suitable inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolinite, sericite, muscovite, synthetic mica, phlogopite, lepidolite, biotite, lithia mica, silicic acid, silicic acid anhydride, aluminum silicate, magnesium silicate, magnesium aluminum silicate, calcium silicate, barium silicate, strontium silicate, metal tungstates, hydroxyapatite, vermiculite, bentonite, montmorillonite, hectolite, zeolite, ceramic powder, calcium hydrogen phosphate, alumina, aluminum hydroxide (e.g., Higilite®), boron nitride, and silica. Of these, zinc oxide, titanium oxide, mica, and sericite are preferred, with zinc oxide and titanium oxide being most preferred.

Pearly pigments and metal powder pigments are also useful as the inorganic powder. Exemplary pearly pigments include titanium oxide-coated mica, bismuth oxychloride, titanium oxide-coated bismuth oxychloride, titanium oxide-coated talc, fish scales, and titanium oxide-coated colored mica. Exemplary metal powder pigments include aluminum powder, copper powder, and stainless steel powder.

Color pigments may also be used. Exemplary color pigments include inorganic red pigments such as iron oxide, iron hydroxide, and iron titanate, inorganic brown pigments such as gamma-iron oxide, inorganic yellow pigments such as yellow iron oxide and yellow ochre, inorganic black pigments such as black iron oxide and carbon black, inorganic purple pigments such as manganese violet and cobalt violet, inorganic green pigments such as chromium hydroxide, chromium oxide, cobalt oxide, and cobalt titanate, inorganic blue pigments such as Prussian blue and ultramarine, lake-formed tar dyes, lake-formed natural dyes, and composite powders thereof.

Suitable organic powders include polyamide powder, polyester powder, polyethylene powder, polypropylene powder, polystyrene powder, polyurethane powder, benzoguanamine powder, polymethylbenzoguanamine powder, tetrafluoroethylene powder, polymethyl methacrylate powder, cellulose powder, silk powder, nylon powder (e.g., nylon 12, nylon 6), silicone powder, silicone composite powder, styrene-acrylic acid copolymers, divinylbenzene-styrene copolymers, vinyl resins, urea resins, phenolic resins, fluoro-resins, silicon resins, acrylic resins, melamine resins, epoxy resins, polycarbonate resins, microcrystalline fiber powder, starch, and lauroyl lysine.

Surface-active metal salts (or metal soaps) may also be used as the organic powder. Examples include zinc stearate, aluminum stearate, calcium stearate, magnesium stearate, zinc myristate, magnesium myristate, zinc cetyl phosphate, calcium cetyl phosphate, and sodium zinc cetyl phosphate.

Tar dyes and natural dyes are also useful as the substrate. Exemplary tar dyes include Red #3, Red #104, Red #106, Red #201, Red #202, Red #204, Red #205, Red #220, Red #226, Red #227, Red #228, Red #230, Red #401, Red #505, Yellow #4, Yellow #5, Yellow #202, Yellow #203, Yellow #204, Yellow #401, Blue #1, Blue #2, Blue #201, Blue #404, Green #3, Green #201, Green #204, Green #205, Orange #201, Orange #203, Orange #204, Orange #206, and Orange #207. Exemplary natural dyes include carminic acid, laccaic acid, carthamin, brazilin, and crocin, all in powder form.

Any of these powdered substrates which are readily available may be employed herein independent of their shape (spherical, needle, plate, etc.), particle size (fumed, microparticulate, pigment grade, etc.), and particle structure (porous or non-porous). The powder may previously be combined with another powder to form a composite or surface treated with a surfactant or water-soluble polymer.

First, the surface of the substrate is treated with the hydrolyzable silyl group-containing acid anhydride compound. This treatment may be performed by any well-known techniques. The basis process involves coating the substrate surface with the treating agent, removing the solvent, and drying. Typical surface treatment of powder may be carried out by dispersing powder particles in a solvent, adding the hydrolyzable silyl group-containing acid anhydride compound to the dispersion, agitating the dispersion, then heating the dispersion. This is followed by solvent removal, drying and baking treatment. After cooling to room temperature, the resulting conglomerate sample is ground in a mortar, yielding a surface treated powder. The amount of the hydrolyzable silyl group-containing acid anhydride compound added is preferably 0.01 to 30 parts by weight, and more preferably 0.1 to 10 parts by weight relative to 100 parts by weight of the powder. Less than 0.01 pbw of the compound may fail to finally hydrophilize the powder to a full extent. When the compound is added in excess of 30 pbw, the hydrophilizing effect may be saturated and no longer enhanced.

Next comes ring-opening of the acid anhydride moiety via hydrolysis and neutralization treatment. This treatment may be performed, for example, by dispersing the surface treated powder (treated as above) in water or a mixture of water and a solvent, adding a base as a catalyst and neutralizing agent to the dispersion, and heating the dispersion while agitating. Although a minimum amount of the base allows the acid anhydride to undergo hydrolysis toward ring-opening, the amount of the base added is preferably a neutralizing equivalent amount which is 0.1 to 2 times, more preferably 0.5 to 1.5 times the total equivalent amount of carboxylic acid resulting from ring-opening of the acid anhydride moiety. Then carboxylic acid resulting from ring-opening of the acid anhydride moiety is partially or completely neutralized with the base whereby the treated powder is improved in surface hydrophilicity and becomes fully dispersible in aqueous media. On the equivalent basis described above, less than 0.1 time equivalent of the base may fail to provide sufficient hydrophilicity. If the base is added in an amount of more than 2 times equivalent, the liquid becomes more basic, which may probably raise inconvenient problems like skin irritation when applied to cosmetics.

The base used herein is not particularly limited and includes alkaline metal hydroxides, alkaline earth metal hydroxides, and organic amines. Examples include NaOH, KOH, $Ca(OH)_2$, $Mg(OH)_2$, ammonia, monoethanolamine, diethanolamine, triethanolamine, and triethylamine. The solvent to be mixed with water is preferably selected from alcohols such as methanol, ethanol, and 2-propanol. The concentration of the surface treated powder dispersed in water or water/solvent mixture is preferably 5 to 50% by weight though not particularly limited.

Finally, the dispersion after hydrolysis and neutralizing treatment is heated for removing the solvent and drying, after which the dry product is ground into the desired hydrophilized particles.

The hydrophilized powder prepared as above is fully dispersible in aqueous media and stable in dispersed state. Then the hydrophilized powder is dispersed in an aqueous medium which is water, a water-soluble solvent, or a mixture of water and a water-soluble solvent to form a dispersion which is advantageously applicable to cosmetics, skin external preparations, paints, inks and the like. Examples of the water-soluble solvent which can be used herein include alcohols such as methanol, ethanol, and 2-propanol, and glycol ethers such as propylene glycol monomethyl ether and dipropylene glycol monomethyl ether. Water and the water-soluble solvent are preferably mixed in a weight ratio between 90:10 and 10:90.

The liquid dispersion may be prepared, for example, by the following method. After the hydrophilized powder is prepared by the aforementioned method, it is added to an aqueous medium such as water or alcohol and fed to a dispersing machine such as a ball mill, bead mill or sand mill where particles are dispersed in the medium.

The following procedure is effective for the simple preparation of a liquid dispersion. In the course of preparing the hydrophilized powder, the powder is dispersed in an aqueous medium which is water or water and solvent, hydrolysis and neutralizing treatment is carried out to complete the hydrophilic treatment of powder surface. Thereafter, the resulting liquid is directly (omitting the solvent removal and drying step) fed to a dispersing machine where it is finely dispersed.

The hydrophilized powder and the dispersion containing the same are advantageously used in cosmetics, paints, aqueous inks, and the like. For use in cosmetics, various ingredients which are commonly used in ordinary cosmetics may be added, for example, solid, semi-solid and liquid oils and fats, water, alcohols, water-soluble polymers, film-forming agents, surfactants, oil-soluble gelling agents, water-soluble gelling agents, organic-modified clay minerals, resins, powders, UV absorbers, humectants, preservatives, germicides, perfumes, salts, antioxidants, pH modifiers, chelating agents, refreshing agents, anti-inflammatory agents, skin-modifying agents (e.g., whitening agents, cell activating agents, anti-skin-roughening agents, hemodynamic accelerators), vitamins, amino acids, nucleic acids, hormones, and inclusion compounds.

EXAMPLE

Examples are given below by way of illustration and not by way of limitation.

Example 1

[1] Surface Treatment of Powder

A 1-L three-neck flask equipped with a stirrer, thermometer, ester adaptor and Dimroth condenser was charged with 50.0 g of titanium oxide powder (MT-100SA by TAYCA Corporation, average primary particle size 15 nm, alumina-silica surface treatment), 3.80 g of water, 3.00 g (1.15×

$10^{-2}$ mole) of a hydrolyzable silyl group-containing acid anhydride compound having the structural formula (3), and 100 g of acetone.

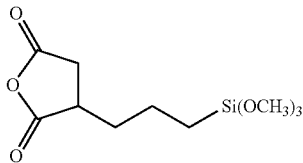
(3)

The contents were mixed and stirred for 30 minutes at room temperature. The flask was heated to about 60° C. for distilling off acetone, after which with stirring interrupted, heat treatment was continued at 105° C. for 3 hours. Cooling to room temperature resulted in a conglomerate sample which was ground on a mortar into particles.

[2] Ring-Opening Due to Hydrolysis of Acid Anhydride Moiety and Neutralization

A 1-L three-neck flask equipped with a stirrer, thermometer, and Dimroth condenser was charged with the entire amount of the surface treated powder, 75.0 g of water, and 3.43 g ($2.30 \times 10^{-2}$ mole, corresponding to equivalent relative to difunctional carboxylic acid resulting from ring opening of the acid anhydride moiety) of triethanolamine. With stirring, the contents were heated at 60° C. for one hour. Cooling to room temperature results in a liquid sample.

[3] Dispersion

A 100-mL glass vial was charged with 100 g of the liquid sample and 200 g of zirconia beads having a diameter of 1-2 mm, closed with a cap, and loaded in a paint shaker. Dispersion treatment was performed for 15 hours.

[4] Evaluation of Dispersion

Using a particle size distribution meter (Nikkiso Co., Ltd.), the size of surface treated particles in the liquid dispersion was measured. The viscosity at 25° C. of the liquid dispersion was measured by a rotational viscometer.

Example 2

The same procedures as in Example 1 were repeated except that the amount of triethanolamine added in stage [2] was changed to 6.86 g ($4.60 \times 10^{-2}$ mole).

Example 3

The same procedures as in Example 1 were repeated except that in stage [1], the powder was changed to zinc oxide powder (MZ-500 by TAYCA Corporation, average primary particle size 20-30 nm, no surface treatment), and the amount of the hydrolyzable silyl group-containing acid anhydride compound having formula (3) was changed to 1.50 g ($5.73 \times 10^{-3}$ mole). In stage [2], 0.58 g ($5.73 \times 10^{-3}$ mole) of triethylamine was added as the base.

Comparative Example 1

The same procedure as in stage [1] of Example 1 was repeated except that 3.00 g of a hydrolyzable silyl group-containing acid anhydride compound having the formula (4):

$$CH_3O(C_2H_4O)_{10}C_3H_6Si(OCH_3)_3 \quad (4)$$

was added. Stage [2] was omitted. A 100-mL glass vial was charged with 40 g of the powder sample from stage [1], 60 g of water, and 200 g of zirconia beads having a diameter of 1-2 mm, closed with a cap, and loaded in a paint shaker. Dispersion treatment was performed for 15 hours. The resulting dispersion was evaluated as in stage [4] of Example 1.

Comparative Example 2

The same procedure as in stage [1] of Example 1 was repeated except that the powder was changed to zinc oxide powder (MZ-500 by TAYCA Corporation, average primary particle size 20-30 nm, no surface treatment), and the amount of the hydrolyzable silyl group-containing acid anhydride compound having formula (3) was changed to 1.50 g ($5.73 \times 10^{-3}$ mole). Stage [2] was omitted. A 100-mL glass vial was charged with 40 g of the powder sample from stage [1], 60 g of water, and 200 g of zirconia beads having a diameter of 1-2 mm, closed with a cap, and loaded in a paint shaker. Dispersion treatment was performed for 15 hours. The resulting dispersion was evaluated as in stage [4] of Example 1.

Table 1 reports the type and amount of powder, surface treating agent, and base as well as a molar ratio of base added to carboxylic acid resulting from ring opening of acid anhydride. Table 2 reports the measurement results.

TABLE 1

| | | Powder | | Surface treating agent | | Base | | |
|---|---|---|---|---|---|---|---|---|
| | | $TiO_2$ powder | ZnO powder | Compound (3) | Compound (4) | triethanol- amine | triethyl- amine | Base/acid (molar ratio) |
| Example | 1 | 50.0 g | — | 3.00 g ($1.15 \times 10^{-2}$ mol) | — | 3.43 g ($2.30 \times 10^{-2}$ mol) | — | 1.00 |
| | 2 | 50.0 g | — | 3.00 g ($1.15 \times 10^{-2}$ mol) | — | 6.86 g ($4.60 \times 10^{-2}$ mol) | — | 2.00 |
| | 3 | — | 50.0 g | 1.50 g ($5.73 \times 10^{-3}$ mol) | — | — | $5.80 \times 10^{-1}$ g ($5.73 \times 10^{-3}$ mol) | 0.50 |
| Comparative Example | 1 | 50.0 g | — | — | 3.00 g | — | — | — |
| | 2 | — | 50.0 g | 1.50 g ($5.73 \times 10^{-3}$ mol) | — | — | — | 0.00 |

TABLE 2

| | Average particle size (μm) | Viscosity (mPa·s) |
|---|---|---|
| Example 1 | 0.113 | 13.5 |
| Example 2 | 0.113 | 11.5 |
| Example 3 | 0.113 | 7.5 |
| Comparative Example 1 | 0.656 | ≥100 |
| Comparative Example 2 | 1.016 | ≥100 |

The powders hydrophilized in Examples 1 to 3 according to the invention are finely dispersible in water as compared with Comparative Examples 1 and 2.

Japanese Patent Application No. 2009-003440 is incorporated herein by reference.

The invention claimed is:

1. A method for preparing a hydrophilized substrate, comprising:
   (A) treating a surface of a substrate with a hydrolyzable silyl group-containing acid anhydride compound having the general formula (1):

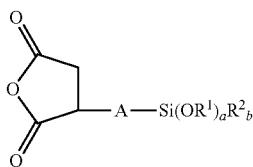

wherein
   $R^1$ is hydrogen or $C_1$-$C_6$ alkyl,
   $R^2$ is each independently an organic group selected from the group consisting of $C_1$-$C_{30}$ alkyl, aryl, aralkyl, and fluoroalkyl,
   A is a straight or branched $C_2$-$C_6$ alkylene,
   a is an integer of 1 to 3,
   b is an integer of 0 to 2, and
   a+b=3,
   (B) immersing the surface treated substrate in water or a mixture of water and a solvent, adding a base thereto, and heating the liquid for thereby hydrolyzing the acid anhydride moiety to open its ring and neutralizing the resultant carboxylic acid, and
   (C) removing water and the solvent until the substrate is dry.

2. The method of claim 1, wherein the acid anhydride compound has the general formula (2):

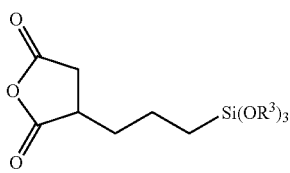

wherein $R^3$ is methyl or ethyl.

3. The method of claim 1, wherein the base is selected from the group consisting of NaOH, KOH, ammonia, monoethanolamine, diethanolamine, triethanolamine, and triethylamine, and mixtures thereof.

4. The method of claim 1, wherein the base is selected from the group consisting of monoethanolamine, diethanolamine, and triethanolamine, and mixtures thereof.

5. The method of claim 1, wherein the base is used in an equivalent amount which is 0.1 to 2 times the total equivalent amount of carboxylic acid resulting from ring-opening of the acid anhydride moiety.

6. The method of claim 1, wherein the substrate is a powder.

7. The method of claim 6, wherein the powder is an inorganic powder.

8. The method of claim 7, wherein the powder is zinc oxide.

9. The method claim 7, wherein the powder is titanium oxide.

10. A method for preparing a dispersion of hydrophilized powder, comprising:
    (A) treating surfaces of powder particles with a hydrolyzable silyl group-containing acid anhydride compound having the general formula (1):

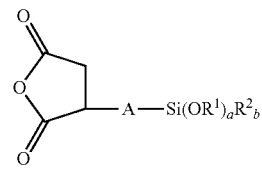

wherein
    $R^1$ is hydrogen or $C_1$-$C_6$ alkyl,
    $R^2$ is each independently an organic group selected from the group consisting of $C_1$-$C_{30}$ alkyl, aryl, aralkyl, and fluoroalkyl,
    A is a straight or branched $C_2$-$C_6$ alkylene,
    a is an integer of 1 to 3,
    b is an integer of 0 to 2, and
    a+b=3,
    (B) immersing the surface treated powder in water or a mixture of water and a solvent, adding a base thereto, and heating the liquid for thereby hydrolyzing the acid anhydride moiety to open its ring and neutralizing the resultant carboxylic acid, and
    (C) feeding the liquid from step (B) to a dispersing machine for finely dispersing the powder particles.

11. The method of claim 10 wherein the acid anhydride compound has the general formula (2):

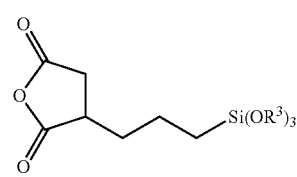

wherein $R^3$ is methyl or ethyl.

12. The method of claim 10, wherein the base is selected from the group consisting of NaOH, KOH, ammonia, monoethanolamine, diethanolamine, triethanolamine, and triethylamine, and mixtures thereof.

13. The method of claim 10, wherein the base is selected from the group consisting of monoethanolamine, diethanolamine, and triethanolamine, and mixtures thereof.

14. The method of claim 10, wherein the base is used in an equivalent amount which is 0.1 to 2 times the total equivalent amount of carboxylic acid resulting from ring-opening of the acid anhydride moiety.

15. The method of claim 10, wherein the powder is an inorganic powder.

16. The method of claim 15, wherein the powder is zinc oxide.

17. The method of claim 15, wherein the powder is titanium oxide.

* * * * *